US012773550B2

(12) United States Patent
Roy

(10) Patent No.: US 12,773,550 B2
(45) Date of Patent: Oct. 27, 2026

(54) FLUORO-LESS SYSTEM AND METHOD FOR DELIVERING CATHETER-BASED BLOOD PUMPS

(71) Applicant: ABIOMED, Inc., Danvers, MA (US)

(72) Inventor: Vincent Roy, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 908 days.

(21) Appl. No.: 17/979,100

(22) Filed: Nov. 2, 2022

(65) Prior Publication Data

US 2023/0134024 A1 May 4, 2023

Related U.S. Application Data

(60) Provisional application No. 63/275,561, filed on Nov. 4, 2021.

(51) Int. Cl.

*A61M 60/867* (2021.01)
*A61M 25/09* (2006.01)
*A61M 60/13* (2021.01)
*A61M 60/857* (2021.01)

(52) U.S. Cl.

CPC .......... *A61M 60/867* (2021.01); *A61M 25/09* (2013.01); *A61M 60/13* (2021.01); *A61M 60/857* (2021.01)

(58) Field of Classification Search

CPC .............. A61M 25/0166; A61M 60/13; A61M 60/867; A61B 34/10; A61B 34/20; A61B 2034/2051

See application file for complete search history.

(56) References Cited

U.S. PATENT DOCUMENTS

2008/0146942 A1 6/2008 Dala-Krishna
2009/0062739 A1 3/2009 Anderson
2011/0034874 A1 2/2011 Reitan et al.
2018/0070855 A1 3/2018 Eichler
2018/0099125 A1* 4/2018 Richer ............ A61M 25/09041
2018/0271402 A1* 9/2018 Osadchy .............. A61B 5/0536
2020/0268953 A1 8/2020 Ferrari et al.

OTHER PUBLICATIONS

International Search Report and Written Opinion for corresponding application PCT/US2022/048660, dated Feb. 14, 2023.
Adam Edward Evard: "Catheter Localization Utilizng a Sensor-Enabled Guidewire Design of a Proof of-Concept System" Thesis presented to the Faculty of California Polytechnic State University; https://digitalcommons.calpoly.edu/theses/2506/; Jun. 2018.
First Exam Report corresponding to IN App. No. 202417041265 issued May 20, 2026.

* cited by examiner

*Primary Examiner* — Laura A Bouchelle
(74) *Attorney, Agent, or Firm* — MEAGHER EMANUEL LAKS GOLDBERG & LIAO, LLP.

(57) ABSTRACT

The disclosed system and method generally involve using guidewire imaging technology to create a three-dimensional image or map of the vessels all the way from an insertion site to the heart. This imaging provides useful landmarks and information about tortuosity and position. The method then measures pump and/or pump catheter position during insertion using direct or indirect techniques. This pump position can then be overlayed onto the three-dimensional image or map created by the guidewire to determine inflow position in the vessel, the proximity to key landmarks, and assist in the delivery without fluoroscopy.

14 Claims, 4 Drawing Sheets

FLUORO-LESS SYSTEM AND METHOD FOR DELIVERING CATHETER-BASED BLOOD PUMPS

CROSS-REFERENCE TO RELATED APPLICATIONS

This application claims priority to U.S. Provisional Patent App. No. 63/275,561, filed Nov. 4, 2021, the entirety of which is incorporated by reference herein.

TECHNICAL FIELD

The present disclosure is drawn to catheter-based blood pumps, and specifically, a blood pumps that can be delivered to a patient without the use of fluoroscopy.

BACKGROUND

Catheter-based blood pumps, and specifically blood pumps intended to be inserted into a patient's heart, are traditionally surgically inserted or implanted into a blood vessel, such as a chamber of a patient's heart, using external imaging equipment. Typically, a guidewire may be inserted via an introducer sheath into, e.g., a femoral or jugular vein, and, typically under fluoroscopy or other similar imaging technique, the guidewire is steered through the patient's vasculature. The blood pump is then advanced along the guidewire, also under fluoroscopy, until the blood pump is in a desired location.

However, using fluoroscopy or other similar technique requires additional scanners and detectors that can add complexity to an already complicated surgery, and fluoroscopy equipment is not always available in every operating room. Therefore, it would be useful to have a simple method for inserting a blood pump that did not rely on fluoroscopy or other similar imaging techniques.

BRIEF SUMMARY

Various deficiencies in conventional techniques are addressed below by the disclosed systems and methods.

A method for the flouro-less delivery of a catheter-based blood pump may be provided. The disclosed method generally involves using guidewire imaging technology to create a three-dimensional image or map of the vessels all the way from an insertion site to the heart. This imaging provides useful landmarks and information about tortuosity and position. The method then measures pump and/or pump catheter position during insertion using direct or indirect technology. This pump position can then be overlayed onto the three-dimensional image or map created by the guidewire to determine inflow position in the vessel, the proximity to key landmarks, and assist in the delivery without fluoroscopy.

More specifically, the method may involve mapping a pathway from an insertion site through one or more blood vessels of a patient (e.g., towards a patient's heart through the patient's vasculature) using a sensor on a guidewire. A catheter including a blood pump may then advanced along the guidewire towards a patient's heart, the catheter passing through an internal lumen of an introducer sheath or a suture hub. During this advancement, bidirectional axial movement and/or rotation of the catheter through the internal lumen may be directly or indirectly measured using a sensor operably connected to the introducer sheath or suture hub. The sensor may be, e.g., a roller encoder, an optical detector (for example, to detecting markings on the catheter as it passes through the internal lumen) or may be configured to measure eddy currents (provided there was an appropriate ferromagnetic material in the catheter). The method may then involve determining a position of the blood pump along the mapped pathway based on the measured bidirectional axial movement of the catheter. With the determined position, at least a portion of the mapped pathway and a representation of the determined position of the blood pump along the mapped pathway can be displayed.

Optionally, the method may also include storing a value representing the position of the blood pump in a fully inserted position on a non-transitory computer readable medium. This can be used when monitoring and tracking the pump position over time, to ensure the pump remains in position. For example, after a blood pump is fully inserted, the position of the blood pump at that time may be stored. Optionally, the method may include measuring additional bidirectional axial movements and/or rotations of the catheter through the internal lumen, and determining, based on the measured additional bidirectional axial movement and/or rotation of the catheter and that stored value, whether the position of the blood pump has changed by more than a predetermined threshold.

In some embodiments, a fluoro-less system for delivering a catheter-based blood pump to a patient may be provided. The system may include at least two components: (i) an introducer sheath or a suture hub with a sensor configured to provide feedback regarding bidirectional axial movement of a catheter comprising a blood pump through an internal lumen configured and dimensioned to slidably receive the catheter; and (ii) at least one processor configured to receive the feedback, and determine a linear position and/or rotational orientation of the blood pump along a pre-mapped pathway within a patient's vasculature based on the feedback.

The system preferably may also include a display. The at least one processor may be configured to send at least one image including the pre-mapped pathway and at least an indication for the location and/or rotational orientation of the blood pump along the pre-mapped pathway.

The system preferably may also include a guidewire with a sensor configured to provide information to the at least one processor, and where the processor(s) may be configured to generate a three-dimensional pathway of the guidewire based on the information, and then may use the generated three-dimensional pathway of the guidewire as the pre-mapped pathway.

Optionally, the at least one processor may be further configured to store a value representing the position and/or orientation of the blood pump after the blood pump has been fully inserted. The value representing the position of the blood pump may comprise, e.g., three-dimensional coordinates, one or more values representing a rotational orientation, or a value representing the linear distance the catheter has moved along the pre-mapped pathway.

Optionally, the one or more processors may be configured to receive feedback regarding bidirectional axial movement and/or rotation of the catheter after the blood pump has been fully inserted, and to track a position of the blood pump over a period of time, which may include the period of time from final insertion until a point in time after the patient is ambulatory.

Optionally, the system may also include at least one wired or wireless transceiver coupled to the at least one processor.

Optionally, the one or more processors may be further configured to determine a difference between a current position of the blood pump and the position of the blood pump when it had first been fully inserted and generate a warning or alert if the difference is greater than a predetermined threshold.

Optionally, the one or more processors may be further configured to determine a difference between a current position of the blood pump and a most recently determined position of the blood pump and generate a warning or alert if the difference is greater than a predetermined threshold.

An introducer sheath for a fluor-less system for delivering a catheter-based blood pump may be provided. The introducer sheath may include a tubular body portion having a proximal region and a distal region, the tubular body portion defining an internal lumen configured and dimensioned to slidably receive a catheter. The sheath also includes a sensor operably connected to the proximal region of the tubular body portion; the sensor configured to provide feedback regarding bidirectional axial movement and/or rotation of the catheter through the tubular body portion. The sensor may be, e.g., a roller encoder or an optical detector, or may be configured to measure eddy currents.

A suture hub may be provided. The suture hub may include a central body portion defining an internal lumen configured and dimensioned to slidably receive a catheter, and a sensor operably connected to the central body portion, the sensor configured to provide feedback regarding bidirectional axial movement and/or rotation of the catheter through the central body portion. The sensor may be, e.g., a roller encoder or an optical detector, or may be configured to measure eddy currents.

BRIEF DESCRIPTION OF DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION

Figure 1:
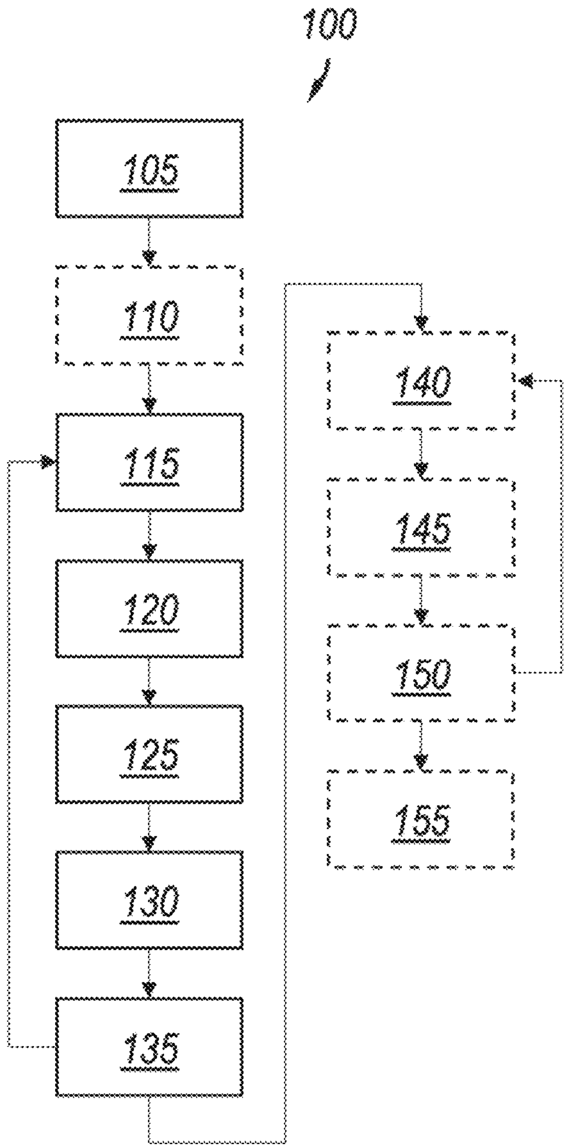
FIG. 1 is a flowchart of an embodiment of the disclosed method.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others.

Various embodiments are directed to system and method for fluoro-less delivery of catheter-based systems, such as catheter-based blood pumps.

In some embodiments, a method for the flouro-less delivery of a catheter-based blood pump may be provided. As seen in FIG. 1, the method 100 may include mapping 105 a pathway from an insertion site towards a patient's heart through the patient's vasculature using a sensor on a guidewire.

In some embodiments, an introducer sheath may be first introduced at an insertion site. The introducer sheath may have a tubular body portion that defines an internal lumen extending from a distal end to a proximal end, configured and dimensioned to slidably receive a catheter. The guidewire can then be inserted through the internal lumen and advanced along the patient's vasculature to create the map.

Specifically, the map may be created based on data received from the sensor. In some embodiments, the map may be a three-dimensional representation of the pathway. In some embodiments, the map may contain sufficient information that a distance along the pathway from the insertion site can be determined.

In some embodiments, the sensor information will be sent to one or more processors, and the one or more processors can make the appropriate calculations based on the sensor information and generate the pathway.

The sensor information can be in any form that would allow a processor to create a three-dimensional pathway from that sensor information. For example, in some embodiments, the sensor information comprises absolute coordinates (such as x, y, z values in a rectangular coordinate system) using the location of the insertion site as the point of origin.

The pathway may be stored on a non-transitory computer readable medium. In some embodiments, the pathway may comprise an ordered series of discrete points, representing the pathway followed by the guidewire.

In some embodiments, method may include optionally displaying 110 the pathway, e.g., on a monitor or other display. The pathway may be represented in any manner appropriate to those of skill in the art, including as individual measured points or a continuous line. In some embodiments, the pathway is overlayed onto visual representations of the patient's vasculature or heart.

In some embodiments, the method may include advancing 115 a catheter-based blood pump along the guidewire (or along a separate guidewire inserted after the pathway has been mapped) towards the patient's heart. In doing so, the catheter may pass through the internal lumen of an introducer sheath or through an internal lumen of a suture hub, e.g., on the catheter-based blood pump.

In some embodiments, the method may include measuring 120 the bidirectional axial movement of the catheter through the appropriate internal lumen using a sensor operably connected to the introducer sheath or the suture hub. That is, a sensor may be used to detect the forward and backward movement and/or rotation of the catheter-based blood pump through the internal lumen, and therefore, may be able to detect the blood pump moving along the pathway defined by the guidewire.

The movement can be quantified and measured using any appropriate means as understood by those of skill in the art. In some embodiments, the movement may be measured directly. For example, the sensor may be a roller encoder that is configured to be in contact with the catheter. As the catheter moves forward and backward, the roller encoder will directly measure both the direction and rate of movement. Alternatively, an eddy current sensor could be used, and as a catheter containing a ferromagnetic material moves past the sensor, movement can be determined, e.g., based on the changing phase and magnitude of the eddy currents.

In other embodiments, the movement may be measured indirectly. For example, the sensor may be an optical detector, and the outer surface of the catheter can be marked with indicators for detection by the sensor. In some embodiments, the sensor may capture a series of images of containing the indicators, and by comparing the change in position of the indicators relative to some point not on the catheter, the movement of the catheter may be determined. In some embodiments, if the indicators include, e.g., a repeating series of three marks, and the sensor is configured to capture an image of a single mark at a time, the detector may be able to determine the direction of movement by the order of the marks that appear, and the rate of movement by the number of frames captured that do not include a recognizable mark.

Once the movement is measured, a position and/or orientation of the blood pump along the mapped pathway may be determined 125 based on the measured bidirectional axial movement of the catheter. In some embodiments, this may be accomplished using one or more processors.

In some embodiments, the one or more processors are configured to have previously determined a partial pathway length for multiple points along the pathway. If the coordinates of points that form the pathway are known, it is straightforward to sum the distances between each pair of points. Some or all of the points along the pathway could have both a set of coordinates and an associated partial pathway length (that is, the pathway length from the insertion site to that point). As movement of the catheter is measured, the one or more processors may determine an insertion distance of the blood pump based on the movement of the catheter—for example, the sum of all detected axial movement plus an offset value, where the offset value could be based on the specific catheter-based blood pump being inserted. In some embodiments, the coordinates of the location of the blood pump could be determined via correlation or interpolation of the total insertion distance with the coordinates of points along the pathway and their determined pathway lengths.

In some embodiments, the method may include displaying 130 at least a portion of the mapped pathway and a representation of the determined position and/or orientation of the blood pump along the mapped pathway. In some embodiments, the entire mapped pathway and the representation of the determined position and/or orientation of the blood pump along the mapped pathway are displayed. In some embodiments, other features of the circulatory system are overlaid on the display as well, including representations of one or more chambers of the heart.

In some embodiments, the method may include determining 135 if the blood pump has reached its target position, and if not, repeating a plurality of steps of the process. Such repeated steps may include advancing, measuring, and determining and displaying positions and/or orientations, is repeated until the blood pump reaches 135 its target position.

If motion after insertion is of interest, additional steps may optionally be taken. For example, after the blood pump has reached its target position, the method may include storing 140 a value, e.g., on a non-transitory computer readable medium, that is representative of the position of the blood pump in a fully inserted target position. This value may be the determined insertion distance or coordinates as discussed previously. However, in preferred embodiments, this value is zero. This minimizes the number of bits required to be stored. This also minimizes the number of calculation steps required to determine how much the blood pump has moved since it reached its target position.

In some embodiments, the method may include measuring 145 any additional bidirectional axial movement and/or rotation of the catheter, just as it was measured during insertion. However, in some embodiments, the introducer sheath may no longer present at a point in time after insertion. Thus, in some embodiments, this post-insertion movement may be measured only if, e.g., a sensor is present on a suture hub.

In some embodiments, the method may include determining 150 a change in a characteristic related to the positioning of the blood pump, and specifically, whether the change is more than a predetermined threshold amount, based on the measured additional bidirectional axial movement and/or rotation of the catheter, and optionally the stored value.

In some embodiments, a single characteristic or change is determined. In some embodiments, a plurality of characteristics or changes is determined.

In some embodiments, this determined change may include the current difference in the forward or backward direction along the pathway from the initial target position of the blood pump. In some embodiments, this may be a sum calculated from a previously stored value plus (or minus) the newly measured additional bidirectional axial movement. This calculated sum may then optionally be stored, e.g., on a non-transitory computer readable medium, to be used in future calculations. It may optionally replace the previously stored value representative of the position of the blood pump. In some embodiments, this threshold is symmetric, such as ±10 mm, ±8 mm, ±6 mm, ±4 mm, or ±2 mm. In some embodiments, the threshold is asymmetric; for example, in some embodiments, the threshold may be +5 mm/−10 mm.

Similarly, in some embodiments, this determined change may include the difference in the forward or backward direction along the pathway relative to a position of the blood pump within a finite time period beforehand. For example, comparing the difference between a position at time t=2 minutes after reaching the target position to a position at time 1 second, 2 seconds, 5 seconds, 10 seconds, or 30 seconds later. This may include comparing the different between a first determined position and the position of the pump at the next time it is determined. For example, if a pump is detected at a position of +0.5 mm, and the next time the pump position is determined the position is −0.5 mm, that may be of concern to a clinician, even if the individual differences from the initial position (here, +0.5 mm and −0.5 mm) of either measurement is acceptable.

In some embodiments, the change to be determined may include whether the absolute total amount of movement of the blood pump, or the absolute amount of movement within a period of time, is above a certain threshold. That is, even if the relative position of the blood pump is within an acceptable distance from the original target position, if the blood pump is moving back-and-forth a great deal, especially within a short period of time, it may be of concern. In some embodiments, there may be a threshold for total movement since the target position was reached. In some embodiments, there may be a threshold for total movement with a window of time where data was collected, such as within any given 5-minute window, any given 1-minute window, or any given 30 second window.

In some embodiments, the change to be determined may include changes to the frequency of movement. For example, if the blood pump inserted into a patient is expected to detect a small movement every second (e.g., 1 Hz), it may be of concern if the blood pump begins to show small movements more rapidly, where the difference in frequency is above a certain threshold. Thus, in some embodiments, the method may include determining if a movement frequency has decreased. In some embodiments, the method may include determining if a movement frequency has increased.

The method may include generating 155 a warning or alert if the change is above a predetermined threshold. The form this warning may take is not particularly limited, and may include, e.g., a visual warning (such as warning lights), an auditory warning (such as a beep alarm), and/or an electronic communication (such as a text message or email message to a doctor, nurse, or other care provider).

Figure 2:
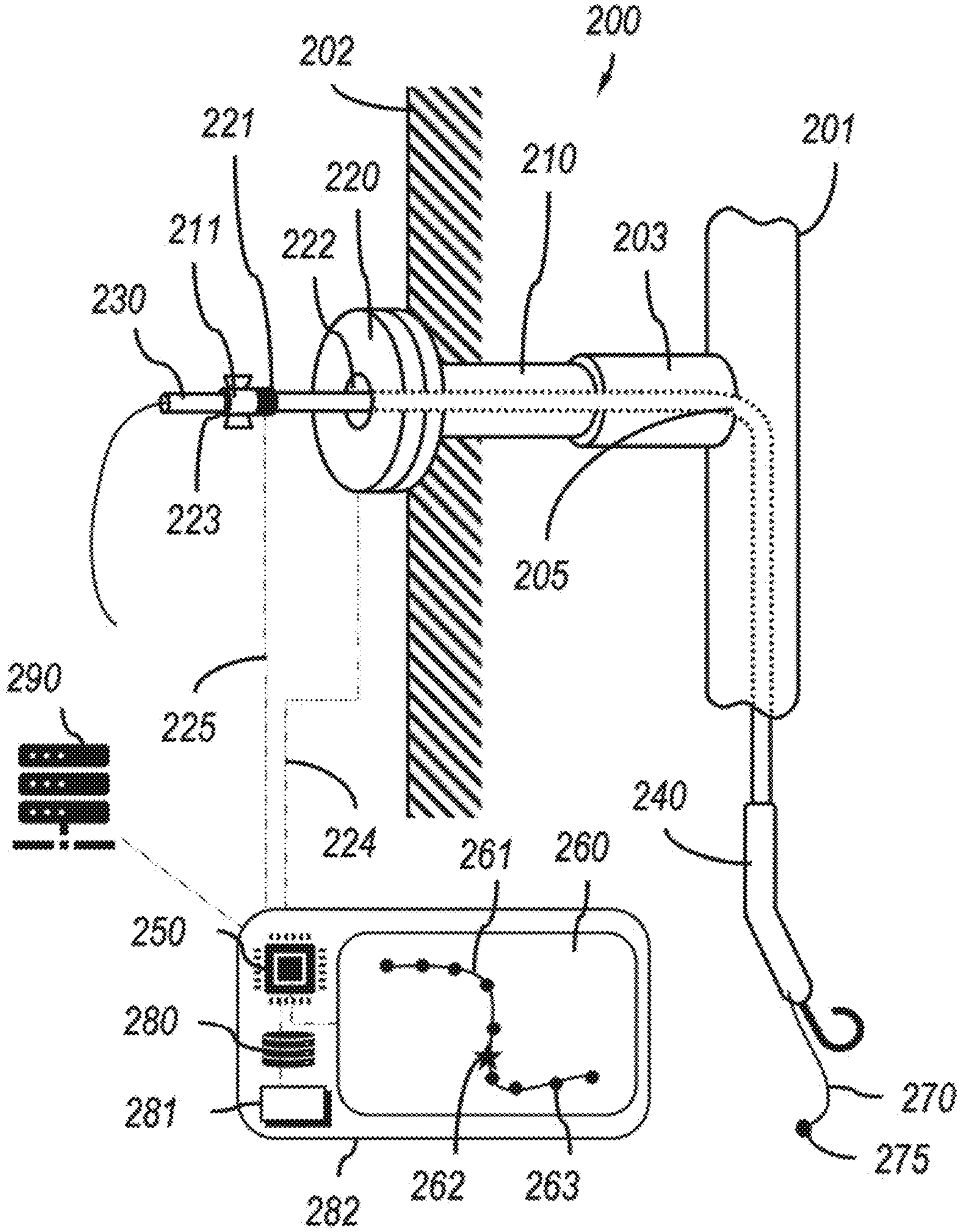
FIG. 2 is a schematic illustrating an embodiment of the disclosed system.

In some embodiments, a fluoro-less system for delivering a catheter-based blood pump to a patient may be provided. An embodiment of such a system can be seen with reference to FIG. 2. There, it can be seen that the system 200 may include an introducer sheath 210 and/or suture hub 211 with at least one sensor 220, 221. The system in FIG. 2 is shown with a sensor on both components, however, other embodiments will function with only one sensor.

The sensor may be configured to provide feedback regarding bidirectional axial movement and/or rotation of a catheter 230 that comprises a blood pump 240 through an internal lumen 222, 223 in the introducer sheath or suture hub that may be configured and dimensioned to slidably receive the catheter.

The system may also include at least one processor 250, preferably coupled to a memory (not shown), that is configured to receive the feedback either wired or wirelessly 224, 225 from the at least one sensor 220, 221 and determine a linear position and/or orientation of the blood pump along a pre-mapped pathway within the vasculature 201 of a patient based on the feedback, as disclosed herein.

The system may also include a display 260, which may be coupled to the one or more processor(s). In some embodiments, the processor(s) may be configured to send at least one image comprising the pre-mapped pathway and at least an indication 262 for the location and/or orientation of the blood pump along the pre-mapped pathway to the display. In some embodiments, the pre-mapped pathway is displayed. In some embodiments, the pre-mapped pathway may include a continuous pre-mapped pathway 261. In some embodiments, the pre-mapped pathway may include a series of points 263 indicating measured points along the pathway may also be displayed as an alternative to, or in addition to, the continuous pre-mapped pathway.

In some embodiments, the pathway may start at an insertion point. In some embodiments, the insertion point is considered to be the point 205 at which the guidewire or catheter would enter the vasculature 201 of the patient. In some embodiments, the insertion point is the point at which the introducer sheath 210 passes into the skin 202 of a patient. In some embodiments, the pathway may include not only a path through the introducer sheath, but also through, e.g., a graft 203.

The system may also include a guidewire 270 comprising a sensor 275 configured to provide information to the at least one processor 250. The at least one processor may be configured to generate a three-dimensional pathway of the guidewire 270 as it passes through the vasculature of a patient based on the provided information, and then use some or all of the generated three-dimensional pathway of the guidewire as the displayed pre-mapped pathway.

In some embodiments, the at least one processor is configured to store (e.g., on non-transitory computer-readable storage medium 280) a value representing the position and/or orientation of the blood pump after the blood pump has been fully inserted. In some embodiments, this value comprises three-dimensional coordinates, or a linear distance the catheter has moved along the pre-mapped pathway, or may be zero.

The system may be configured to determine when the blood pump has been fully inserted in numerous ways. In one embodiment, the system has a button or switch that can be pressed when the blood pump is positioned as desired. The at least one processor may receive input from that button or switch and may optionally change from an insertion phase to an ongoing monitoring phase. In another embodiment, the at least one processor may monitor the insertion process of the blood pump. The processor(s) may determine that the insertion process has started as the point at which the sensor first started detecting continuous forward motion along the pathway. In some embodiments, when the position of the blood pump has remained substantially static (that is, detected movement is zero plus or minus a small amount, such as ±1 mm) for a predetermined period of time (such as five minutes), the processor(s) may automatically determine the insertion process has finished. In some embodiments, a button (not shown) operably coupled to the processor may be used by, e.g., a clinician, to indicate the insertion process has finished.

In some embodiments, the at least one processor may be configured to provide ongoing monitoring of the blood pump's position and/or orientation. In this type of monitoring, the processor(s) may be configured to continue to receive feedback regarding bidirectional axial movement and/or rotation of the catheter, after the blood pump has been fully inserted. The processor(s) may be configured to track the position and/or orientation of the blood pump over a period of time. This period of time may be for a day or two after the blood pump has been inserted, until after the patient is ambulatory, or even longer. In some embodiments, the position and/or orientation of the blood pump is tracked while the patient is ambulatory.

The system may optionally include a wired or wireless transceiver 281 coupled to the at least one processor 250. In some embodiments, some or all of the electronic components (e.g., the at least one processor 250, display 260, storage such as a non-transitory computer-readable storage medium 280, and wired or wireless transceiver 281) are at least partially enclosed in a single housing 282.

In some embodiments, the one or more processor(s) may also include at least one processor on a remote server 290, which as understood in the art may include a remote processor, memory, and non-transitory computer-readable storage medium (not shown). In some embodiments, the one or more processor(s) present locally are configured to operatively communicate with the remote server. In some embodiments, some or all of the data gathered by the sensors is stored on a non-transitory computer-readable storage medium coupled to the remote server.

In some embodiments, non-transitory computer-readable storage medium 280 may include instructions that, when executed by the at least one processor 250, configures the one or more processors to perform some or all of the method disclosed herein. For example, in some embodiments, the one or more processors may be configured to determine a difference between a current position of the blood pump and a previous position, such as the position of the blood pump when it had first been fully inserted, and then generate a warning or alert if the difference is greater than a predetermined threshold. In some embodiments, the one or more processors may be further configured to determine a difference between a current position of the blood pump and a most recently determined position of the blood pump, and then generate a warning or alert if the difference is greater than a predetermined threshold. As disclosed herein, the warning may be visual (e.g., on the display) or audio (e.g., using a speaker (not shown)) warning or alert, and/or may involve a communication being sent, such as a text message or email.

Figure 3:
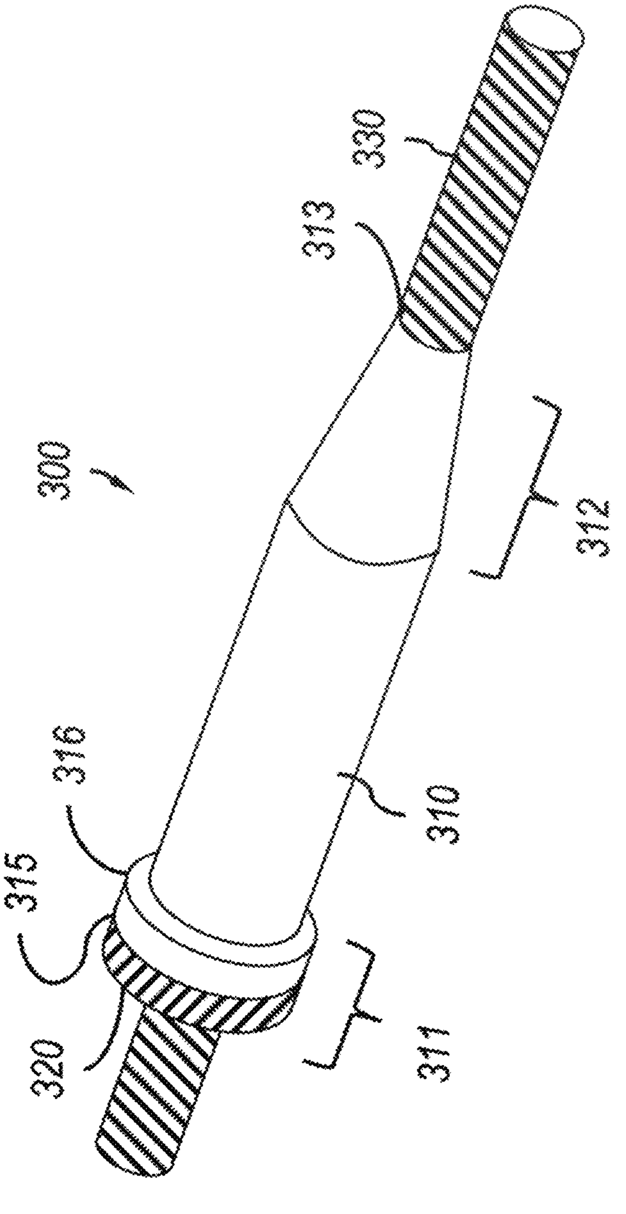
FIG. 3 is an illustration of an embodiment of a disclosed introducer sheath.

An introducer sheath for a fluor-less system for delivering a catheter-based blood pump may be provided. An embodiment of an introducer sheath can be understood with reference to FIG. 3. In some embodiments, the introducer sheath 300 may include a tubular body portion 310 having a proximal region 311 and a distal region 312. The tubular body portion may define an internal lumen 313 configured and dimensioned to slidably receive a catheter 330. The internal lumen may extend longitudinally through the introducer sheath. The tubular body portion is preferably formed from a medical grade natural or synthetic rubber or a plastic such as fluorinated ethylene-propylene (FEP), polyethylene (PE), or the like.

In some embodiments, the introducer sheath may include a sensor 320 operably connected to the tubular body portion. In some embodiments, the sensor may be operably connected to the proximal region of the tubular body portion. In some embodiments, some or all of the sensor may be attached to the proximal-most surface 315 of the tubular body portion. In some embodiments, the sensor may be operably connected to the distal region of the tubular body portion. In some embodiments, some or all of the sensor may be attached to the distal-most surface of the tubular body portion. In some embodiments, some or all of the sensor may be positioned within the internal lumen 313.

The proximal region may include a hub 316 at the proximal end of the tubular body portion. The hub may be configured to allow insertion of devices into the introducer sheath, through the internal lumen.

In some embodiments, the sensor may be configured to provide feedback regarding bidirectional axial movement and/or rotation of the catheter through the tubular body portion. In some embodiments, the sensor may include a roller encoder. In some embodiments, the sensor may include an optical detector. In some embodiments, the sensor may include an eddy current sensor. In some embodiments, the sensor may include a roller encoder, an optical detector, an eddy sensor, or any combination thereof.

Figure 4:
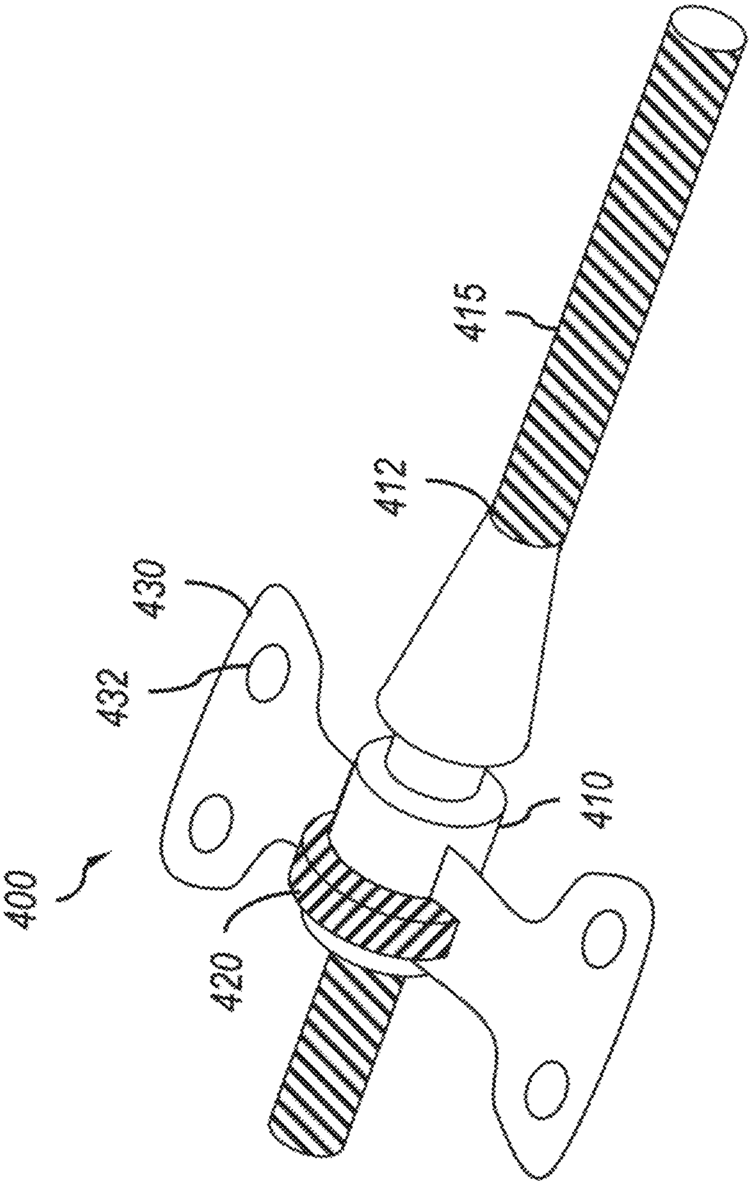
FIG. 4 is an illustration of an embodiment of a disclosed suture hub.

A suture hub for a fluor-less system for delivering a catheter-based blood pump may be provided. An embodiment of a suture hub may be described with reference to FIG. 4. In some embodiments, the suture hub 400 may include a central body portion 410 defining an internal lumen 412 that may be configured and dimensioned to slidably receive a catheter 415. The central body portion may preferably be formed from a medical grade natural or synthetic rubber or a plastic such as fluorinated ethylene-propylene (FEP), polyethylene (PE), or the like.

In some embodiments, the suture hub may include a sensor 420. In some embodiments, the sensor may be operably connected to the central body portion. In some embodiments, some or all of the sensor may be positioned within the internal lumen 412. In some embodiments, some or all of the sensor may be attached to a proximal end of the central body portion. In some embodiments, the sensor may be attached to a distal end of the central body portion.

In some embodiments, the sensor may be configured to provide feedback regarding bidirectional axial movement and/or rotation of the catheter through the tubular body portion. In some embodiments, the sensor may include a roller encoder. In some embodiments, the sensor may include an optical detector. In some embodiments, the sensor may include an eddy current sensor. In some embodiments, the sensor may include a roller encoder, an optical detector, an eddy sensor, or any combination thereof.

In some embodiments, the suture hub may include one or more wings 430, coupled to the central body portion. In some embodiments, each wing may define one or more lumens 432 extending through the wing.

Those skilled in the art will recognize or be able to ascertain using no more than routine experimentation, many equivalents to the specific embodiments of the invention described herein. Such equivalents are intended to be encompassed by the following claims.

What is claimed:

1. A method for flouro-less delivery of a catheter-based blood pump, comprising:

mapping a pathway from an insertion site through one or more blood vessels of a patient, using a first sensor on a guidewire;

measuring bidirectional axial movement and/or rotation of a catheter comprising a blood pump using a second sensor operably connected to an introducer sheath and/or a suture hub, the catheter moving along the guidewire through an internal lumen of the introducer sheath and/or suture hub, the internal lumen configured and dimensioned to slidably receive the catheter;

determining a position of the blood pump along the mapped pathway based on the measured bidirectional axial movement and/or rotation of the catheter; and displaying at least a portion of the mapped pathway and a representation of the determined position of the blood pump along the mapped pathway.

2. The method according to claim 1, further comprising storing a value representative of the position of the blood pump in a fully inserted target position.

3. The method according to claim 1, further comprising:

measuring additional bidirectional axial movement and/or rotation of the catheter through the internal lumen of the suture hub after the blood pump is in a fully inserted position; and determining, based on the measured additional bidirectional axial movement and/or rotation of the catheter, whether the position of the blood pump has changed by more than a predetermined threshold.

4. A fluoro-less system for delivering a catheter-based blood pump to a patient, comprising:

an introducer sheath or a suture hub with a sensor configured to provide feedback regarding bidirectional axial movement and/or rotation of a catheter comprising a blood pump through an internal lumen configured and dimensioned to slidably receive the catheter; and at least one processor configured to;

receive the feedback and determine a linear position and/or orientation of the blood pump along a pre-mapped pathway within a patient's vasculature based on the feedback; and determine a difference between a current position of the blood pump and the position of the blood pump when it had first been fully inserted and generate a warning or alert if the difference is greater than a predetermined threshold.

5. The fluoro-less system according to claim 4, further comprising a display, and wherein the at least one processor is further configured to send at least one image comprising the pre-mapped pathway and at least an indication for a location and/or orientation of the blood pump along the pre-mapped pathway to the display.

6. The fluoro-less system according to claim 4, further comprising:

a guidewire, the guidewire comprising a sensor configured to provide information to the at least one processor, wherein the at least one processor is further configured to generate a three-dimensional pathway of the guidewire based on the information, and then use the generated three-dimensional pathway of the guidewire as the pre-mapped pathway.

7. The fluoro-less system according to claim 4, wherein the at least one processor is further configured to store a value representing the position of the blood pump after the blood pump has been fully inserted.

8. The fluoro-less system according to claim 7, wherein the value representing the position of the blood pump comprises three-dimensional coordinates.

9. The fluoro-less system according to claim 7, wherein the value representing the position of the blood pump comprises a value representing a linear distance the catheter has moved along the pre-mapped pathway.

10. The fluoro-less system according to claim 4, wherein the at least one processor is further configured to receive feedback regarding bidirectional axial movement and/or rotation of the catheter after the blood pump has been fully inserted, and a position of the blood pump is tracked over a period of time.

11. The fluoro-less system according to claim 10, wherein the position of the blood pump is configured to be tracked while the patient is ambulatory.

12. The fluoro-less system according to claim 4, wherein the system further comprises a wired or wireless transceiver coupled to the at least one processor.

13. The fluoro-less system according to claim 4, wherein the at least one processor is further configured to:

determine a difference between a current position of the blood pump and a most recently determined position of the blood pump; and generate a warning or alert if the difference is greater than a predetermined threshold.

14. A fluoro-less system for delivering a catheter-based blood pump to a patient, comprising:

an introducer sheath or a suture hub with a sensor configured to provide feedback regarding bidirectional axial movement and/or rotation of a catheter comprising a blood pump through an internal lumen configured and dimensioned to slidably receive the catheter; and at least one processor configured to:

receive the feedback and determine a linear position and/or orientation of the blood pump along a pre-mapped pathway within a patient's vasculature based on the feedback;

determine a difference between a current position of the blood pump and a most recently determined position of the blood pump; and generate a warning or alert if the difference is greater than a predetermined threshold.

* * * * *